US008431746B2

(12) United States Patent
Jacobs

(10) Patent No.: US 8,431,746 B2
(45) Date of Patent: Apr. 30, 2013

(54) METHOD FOR PRODUCING DIPHENYLMETHANE DIAMINE

(75) Inventor: Johannes Jacobs, Ossendrecht (NL)

(73) Assignee: BASF SE, Ludwigshafen (DE)

( * ) Notice: Subject to any disclaimer, the term of this patent is extended or adjusted under 35 U.S.C. 154(b) by 246 days.

(21) Appl. No.: 12/992,472

(22) PCT Filed: May 20, 2009

(86) PCT No.: PCT/EP2009/056118
§ 371 (c)(1),
(2), (4) Date: Nov. 12, 2010

(87) PCT Pub. No.: WO2009/153122
PCT Pub. Date: Dec. 23, 2009

(65) Prior Publication Data
US 2011/0065960 A1    Mar. 17, 2011

(30) Foreign Application Priority Data

May 26, 2008 (EP) .................... 08156927

(51) Int. Cl.
*C07C 211/50* (2006.01)
*C07C 209/82* (2006.01)
*C07C 209/86* (2006.01)

(52) U.S. Cl.
USPC .......................................... 564/333; 564/334

(58) Field of Classification Search .................. 564/333, 564/334
See application file for complete search history.

(56) References Cited

U.S. PATENT DOCUMENTS 4,087,459 A * 5/1978 Knofel et al. ................. 564/331
6,433,219 B1    8/2002 Stroefer et al.

FOREIGN PATENT DOCUMENTS

WO    99 40059    8/1999
WO    99 54289    10/1999

OTHER PUBLICATIONS

International Search Report issued Nov. 16, 2009 in PCT/EP09/056118 filed May 20, 2009.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The invention relates to a process for preparing mixtures of diphenylmethanediamine and polyphenylenepolymethylenepolyamines, which comprises the steps
a) reaction of aniline with formaldehyde in the presence of hydrochloric acid,
b) neutralization of the reaction mixture formed in step a)
c) separation of the organic phase from the aqueous phase,
d) work-up of the organic phase,
e) work-up of the aqueous phase,
wherein step e) comprises at least the steps
e1) extraction of the aqueous phase with an organic solvent,
e2) stripping of the aqueous phase obtained in step e1),
e3) absorption of the solution obtained from step e2).

8 Claims, No Drawings

METHOD FOR PRODUCING DIPHENYLMETHANE DIAMINE

The preparation of diphenylmethanediamine (MDA) by reaction of aniline with formaldehyde in the presence of an acid is known and has been described widely. In industrial practice, the diphenylmethanediamine prepared in this way is always obtained in admixture with more highly condensed polyphenylenepolymethylenepolyamines. In the following, the "MDA" will refer to the mixture of two-ring diphenylmethanediamine and more highly condensed polyphenylenepolymethylenepolyamines.

In industry, the MDA is usually converted into dipenylmethane diisocyanate MDI by reaction with phosgene.

The preparation of MDA is, as described, carried out industrially by reaction of aniline with formaldehyde in the presence of an acid. Hydrochloric acid is usually used as acid. Such processes are generally known and are described, for example, in Kunststoffhandbuch, volume 7, Polyurethane, Carl Hanser Verlag, Munich, Vienna, 3rd edition, 1993, pages 76 to 86, and in a large number of patent applications, for example WO 99/40059.

Variation of the ratio of acid to aniline and of formaldehyde to aniline enables the proportion of the 2-ring product in the MDA to be set as desired.

After the condensation, the acid catalyst is neutralized, usually by addition of sodium hydroxide. Separation of the organic phase, which comprises predominantly MDA, from the aqueous phase, which is an aqueous solution of the salt formed in the neutralization, occurs here.

The organic phase is usually worked up and reacted with phosgene to form the corresponding isocyanate. The work-up is usually carried out by removal of impurities, for example the salt formed in the neutralization, for example by washing with water, and subsequent distillation to remove the water.

The aqueous phase usually still comprises organic constituents. A measure for reporting the organic constituents is the content of organically bound carbon, usually referred to in industry as TOC.

These organic constituents can present problems in the use of the salt solution, for example in the separation of the salts or the production of chlorine from the salt solution.

In industrial practice, the organic constituents are separated off by, for example, washing or extraction. However, the proportions of organic compounds are usually still too high.

It was an object of the present invention to develop a process for preparing MDA in which an aqueous phase which has a very low content of organic compounds is formed. In particular, the content of organically bound carbon (TOC) should be less than 25 ppm.

The object has been able to be achieved by a multistage work-up.

The invention accordingly provides a process for preparing mixtures of diphenylmethanediamine and polyphenylenepolymethylenepolyamines, which comprises the steps a) reaction of aniline with formaldehyde in the presence of hydrochloric acid,
b) neutralization of the reaction mixture formed in step a),
c) separation of the organic phase from the aqueous phase,
d) work-up of the organic phase,
e) work-up of the aqueous phase,
wherein step e) comprises at least the steps
e1) extraction of the aqueous phase with an organic solvent,
e2) stripping of the aqueous phase obtained in step e1),
e3) absorption of the solution obtained from step e2).

Preference is given to using a mineral acid, in particular hydrochloric acid, as acid.

The preparation of MDA in step a) is carried out, as described above, by reacting aniline with formaldehyde in the presence of acids as catalysts. Such processes are generally known and are described, for example, in Kunststoffhandbuch, volume 7, Polyurethane, Carl Hanser Verlag, Munich, Vienna, 3rd edition, 1993, pages 76 to 86, and in a large number of patent applications, for example WO 99/40059.

In place of or in admixture with formaldehyde, it is also possible to use at least one formaldehyde-releasing compound. In particular, the formaldehyde is used as aqueous formalin solution, alcoholic formalin solution, hemiacetal, methyleneimine of a primary amine or N,N'-methylenediamine of a primary or secondary amine or else paraformaldehyde.

The process of the invention can be carried out continuously, semicontinuously or batchwise, preferably continuously or semicontinuously.

In a continuous process, the reactants are metered in the desired ratio to one another into a reactor and an amount of reaction product corresponding to the feed stream is taken from this reactor. Reactors used are, for example, tube reactors. In a batch process or semicontinuous process, the reactants are metered into a batch reactor which is preferably provided with a stirrer and/or a pumped circuit and from which the fully reacted reaction product is taken and passed to work-up.

The process of the invention is preferably carried out at a molar ratio of aniline to formaldehyde of greater than 2. The molar ratio of acid to aniline is preferably greater than 0.05. At these ratios, there is increased formation of the respective two-ring products in the reaction mixture.

The reaction is preferably carried out at a temperature in the range from 0 to 200° C., preferably from 20 to 150° C. and in particular from 40 to 120° C. It has been found that the proportion of the 2,2' and 2,4' isomers in the reaction product increases with increasing temperature.

The pressure in the reaction is 0.1-50 bar absolute, preferably 1-10 bar absolute.

When the reaction is carried out batchwise or semicontinuously, the reaction mixture can be subjected to aging after all the starting materials have been introduced. For this purpose, the reaction mixture is left in the reactor or transferred to another, preferably stirred reactor. The temperature of the reaction mixture is in this case preferably above 75° C., in particular in the range from 110 to 150° C.

The preparation in step a) is followed by the neutralization b) of the reaction mixture. For this purpose, an alkali, preferably sodium hydroxide, is added to the reaction mixture. The combination of the alkali with the reaction mixture is usually carried out in a suitable mixing apparatus such as a stirred vessel, a tube which may, if appropriate, be provided with static mixing elements or other apparatuses. The addition of the alkali effects neutralization of the reaction mixture and thus formation of two immiscible phases, namely the aqueous phase and the organic phase. The neutralization is carried out at an average temperature of from 40 to 120° C. and a pressure of from 1 to 10 bar absolute.

The mixture from step b) is, as described, present as an organic phase and an aqueous phase. These phases are separated in step c). The phases can, for example, be separated from one another by decantation. The respective phases are then worked up separately.

The organic phase separated off in step c), which comprises predominantly MDA with residual amounts of water, ammonia and the starting materials for the preparation of MDA, is worked up in step d). This is effected, for example, by single or multiple washing with water or preferably by multiple distillation to separate off, for example, aniline and water.

The MDA prepared by the process of the invention is usually reacted with phosgene to form MDI. Such processes are generally known and have been described widely, for example in Kunststoffhandbuch, volume 7, Polyurethane, Carl Hanser Verlag, Munich, Vienna, 3rd edition, 1993, pages 76 to 86, and in a large number of patent applications, for example WO 99/40059 or WO 99/54289.

The aqueous phase, which consists essentially of water, the salt of the acid used as catalyst dissolved therein, and traces of the starting materials aniline and formaldehyde and also the end product MDA and further organic compounds, is worked up further in step e).

For this purpose, it is firstly subjected to an extraction with an organic solvent e1). The organic solvents are usually ones which do not react with the constituents of the aqueous phase. Preference is given to using aromatic solvents, for example toluene.

Aniline and MDA still comprised in the aqueous phase are usually separated off. The extraction is preferably carried out in an extraction column. The aqueous phase is passed to further treatment, and the organic phase is separated, with the toluene being recirculated to the extraction and the aniline which is separated off and TDA are recirculated to the process.

The extraction is preferably carried out at a temperature of 50-100° C. The extraction can be carried out at atmospheric pressure or at superatmospheric or subatmospheric pressure, for example at atmospheric pressure.

The aqueous phase from step e1) is then subjected to stripping e2). Stripping can be carried out by means of steam or an inert gas, for example nitrogen. Preference is given to using steam.

Stripping is preferably carried out at a temperature in the range 150-50° C., preferably 110-70° C. Stripping is preferably carried out at atmospheric pressure or slightly superatmospheric or subatmospheric pressure, in particular at atmospheric pressure.

Stripping is followed by adsorption. As adsorbents, it is possible to use zeolites, organic adsorbent resins or activated carbon. Preference is given to using activated carbon. The adsorbent is preferably arranged as a fixed bed. Preference is given to arranging a plurality of these fixed-bed adsorbents in parallel.

The regeneration of the adsorbent can be carried out, for example, by thermal treatment.

After the adsorption, the aqueous phase usually has a content of organic compounds of not more than 25 ppm.

In a preferred embodiment of the invention, the adsorption can be followed by an oxidative treatment of the aqueous phase. This can be carried out, for example, by treatment with ozone, with peroxides, in particular hydrogen peroxide, or with hypochlorites. The content of organic constituents can be reduced further in this way.

In a further embodiment of the invention, a crystallization can be carried out after step e3). The crystallization can comprise part or all of the dissolved salt.

The aqueous solution then preferably has a salt content of 10-30% by weight, preferably 15-20% by weight.

The aqueous solution which has been treated in this way can be used further without problems. Thus, it can be fed to an electrolysis for the production of chlorine or, for example, also be used as coolant.

Salt, in particular sodium chloride, can be produced from the solution.

The process can be added without problems to any existing process for preparing MDA.

The invention claimed is:

1. A process for preparing mixtures of diphenyl-methanediamine and polyphenylenepolymethylenepolyamines, which comprises the steps
    a) reaction of aniline with formaldehyde in the presence of hydrochloric acid,
    b) neutralization of the reaction mixture formed in step a),
    c) separation of the organic phase from the aqueous phase,
    d) work-up of the organic phase,
    e) work-up of the aqueous phase,
        wherein step e) comprises at least the steps
            e1) extraction of the aqueous phase with an organic solvent,
            e2) stripping of the aqueous phase obtained in step e1),
            e3) adsorption of the solution obtained from step e2).

2. The process according to claim 1, wherein step e3) is followed by step e4) an oxidative treatment of the solution.

3. The process according to claim 1, wherein toluene is used as organic solvent in step e1).

4. The process according to claim 1, wherein the stripping in step e2) is carried out using steam.

5. The process according to claim 1, wherein activated carbon is used as an adsorbent in step e3).

6. The process according to claim 1, wherein the adsorption is accomplished with an adsorbent in step e3) and wherein the adsorbent is arranged as a fixed bed.

7. The process according to claim 2, wherein the oxidative treatment in step e4) is carried out using ozone, peroxides and/or hypochlorites.

8. The process according to claim 1, wherein the aqueous phase after step e3) has a content of organically bound carbon of less than 25 ppm.

* * * * *